United States Patent
David et al.

(10) Patent No.: US 11,313,000 B2
(45) Date of Patent: *Apr. 26, 2022

(54) COMPOSITIONS AND METHODS FOR MEASURING BACTERIAL GROWTH

(71) Applicant: DUKE UNIVERSITY, Durham, NC (US)

(72) Inventors: Lawrence David, Durham, NC (US); Rachael Bloom, Durham, NC (US)

(73) Assignee: Duke University, Durham, NC (US)

( * ) Notice: Subject to any disclaimer, the term of this patent is extended or adjusted under 35 U.S.C. 154(b) by 148 days.

This patent is subject to a terminal disclaimer.

(21) Appl. No.: 16/323,203

(22) PCT Filed: Aug. 4, 2017

(86) PCT No.: PCT/US2017/045608
§ 371 (c)(1),
(2) Date: Feb. 4, 2019

(87) PCT Pub. No.: WO2018/027185
PCT Pub. Date: Feb. 8, 2018

(65) Prior Publication Data
US 2019/0169680 A1 Jun. 6, 2019

Related U.S. Application Data

(60) Provisional application No. 62/370,817, filed on Aug. 4, 2016.

(51) Int. Cl.
*C12Q 1/689* (2018.01)
*G01N 33/569* (2006.01)
(Continued)

(52) U.S. Cl.
CPC ............. *C12Q 1/689* (2013.01); *C12Q 1/04* (2013.01); *C12Q 1/06* (2013.01); *C12Q 1/6851* (2013.01);
(Continued)

(58) Field of Classification Search
None
See application file for complete search history.

(56) References Cited

U.S. PATENT DOCUMENTS

2009/0136953 A1  5/2009  Gold et al.
2010/0233686 A1  9/2010  Higuchi et al.
(Continued)

FOREIGN PATENT DOCUMENTS

WO  2016085632 A2  6/2016

OTHER PUBLICATIONS

Martin, M.J. et al. Innovative Food Science and Emerging Technologies 27:15-25 (2015; online Oct. 17, 2014). (Year: 2014).*
(Continued)

*Primary Examiner* — Diana B Johannsen
(74) *Attorney, Agent, or Firm* — Polsinelli PC

(57) ABSTRACT

The invention disclosed herein relates generally to the fields of microbiology, ecology and microfluidics. Particularly, the invention disclosed herein provides compositions and methods for isolating bacteria from complex microbial communities and measuring growth rates of the isolated bacteria in a given environmental condition.

12 Claims, 8 Drawing Sheets

Specification includes a Sequence Listing.

(51) Int. Cl.
| | |
|---|---|
| *C12Q 1/04* | (2006.01) |
| *C12Q 1/06* | (2006.01) |
| *C12Q 1/6851* | (2018.01) |
| *C12Q 1/6853* | (2018.01) |
| *G01N 1/28* | (2006.01) |

(52) U.S. Cl.
CPC ............. *C12Q 1/6853* (2013.01); *G01N 1/28* (2013.01); *G01N 33/56911* (2013.01); *C12Q 2531/113* (2013.01); *C12Q 2600/158* (2013.01)

(56) References Cited

U.S. PATENT DOCUMENTS

| | | | |
|---|---|---|---|
| 2013/0011374 | A1 | 1/2013 | Luquet et al. |
| 2014/0179726 | A1 | 6/2014 | Bajaj et al. |
| 2014/0208832 | A1 | 7/2014 | Hansen et al. |
| 2016/0312275 | A1 | 10/2016 | Blainey et al. |
| 2019/0241943 | A1* | 8/2019 | Villa .................... C12Q 1/6851 |

OTHER PUBLICATIONS

Liu, X. et al. Lab Chip 16:1636 (Apr. 2016). (Year: 2016).*
Eun, Y-J. et al. ACS Chem. Biol. 6:260 (Dec. 2010). (Year: 2010).*
International Search Report PCT/US2017/045608, dated Oct. 27, 2017.
Bachmann, et al., "Availability of public goods shapes the evolution of competing metabolic strategies," PNAS, 2013, 110(35):14302-7.
Cordero, et al, "Ecological Populations of Bacteria Act as Socially Cohesive Units of Antibiotic Production and Resistance," Science, vol. 337, 1228-1231, 2012.
Donia, Cimermancic, et al., "A Systematic Analysis of Biosynthetic Gene Clusters in the Human Microbiome Reveals a Common Family of Antibiotics," Cell 158, 1402-1414, Sep. 11, 2014.
Eckburg, Bik, et al, "Diversity of the Human Intestinal Microbial Flora," 2005 Science, vol. 308, 1635-1638.
Koch, "Oligotrophs versus copiotrophs," 2001 BioEssays, 23(7): 657-661.
Kolter and Moreno "Genetics of Ribosomally Synthesized Peptide Antibiotics," Annu. Rev. Microbiol. 1992. 46:141-63.
Kostic, Gevers et al. "Genomic analysis identifies association of Fusobacterium with colorectal carcinoma," 2012, Genome Research,22:292-298.
Ley, et al., "Human gut microbes associated with obesity," Nature , vol. 444, Dec. 2006, pp. 1022-1023.
Ley, et al."Ecological and Evolutionary Forces Shaping Microbial Diversity in the Human Intestine," Cell 124, 837-848, Feb. 24, 2006.
Ma, et al., "Online Gambling Behavior: The Impacts of Cumulative Outcomes, Recent Outcomes, and Prior Use," Information Systems Research vol. 25, No. 3, Sep. 2014, pp. 511-527.
Maltby, et al, "Nutritional Basis for Colonization Resistance by Human Commensal *Escherichia coli* Strains HS and Nissle 1917 against *E. coli* O157:H7 in the Mouse Intestine," PLoS ONE 8(1): e53957. doi:10.1371/journal. pone.0053957, 2013.
Nichols, et al., "Use of Ichip for High-Throughput In Situ Cultivation of "Uncultivable" Microbial Species," Applied and Environmental Microbiology, Apr. 2010, p. 2445-2450 vol. 76, No. 8.
Rea, et al., "Thuricin CD, a posttranslationally modified bacteriocin with a narrow spectrum of activity against Clostridium difficile," PNAS, 107(20): 9352-9357, May 2010.
Robinson, et al. "From Structure to Function: the Ecology of Host-Associated Microbial Communities," Microbiology and Molecular Biology Reviews, Sep. 2010, p. 453-476 vol. 74, No. 3.
Sartor "Microbial Influences in Inflammatory Bowel Diseases," GASTROENTEROLOGY 2008;134:577-594.
Tumbaugh, Ley et al."An obesity-associated gut microbiome with increased capacity for energy harvest," Nature, vol. 444, Dec. 2006, doi:10.1038/nature05414.
Turnbaugh, et al., "A core gut microbiome in obese and lean twins," Nature, vol. 457, Jan. 2009, doi: 10.1038/nature075402009.
Vetsigian, "Structure and Evolution of Streptomyces Interaction Networks in Soil and In Silico," 2011 PLoS Biol 9(10): e1001184.
Goel et al., "Standardized Assay Medium To Measure Lactococcus lactis Enzyme Activities while Mimicking Intracellular Conditions," Appl Evbiron Microbiol, 2012, 78(1): 134-143.

* cited by examiner

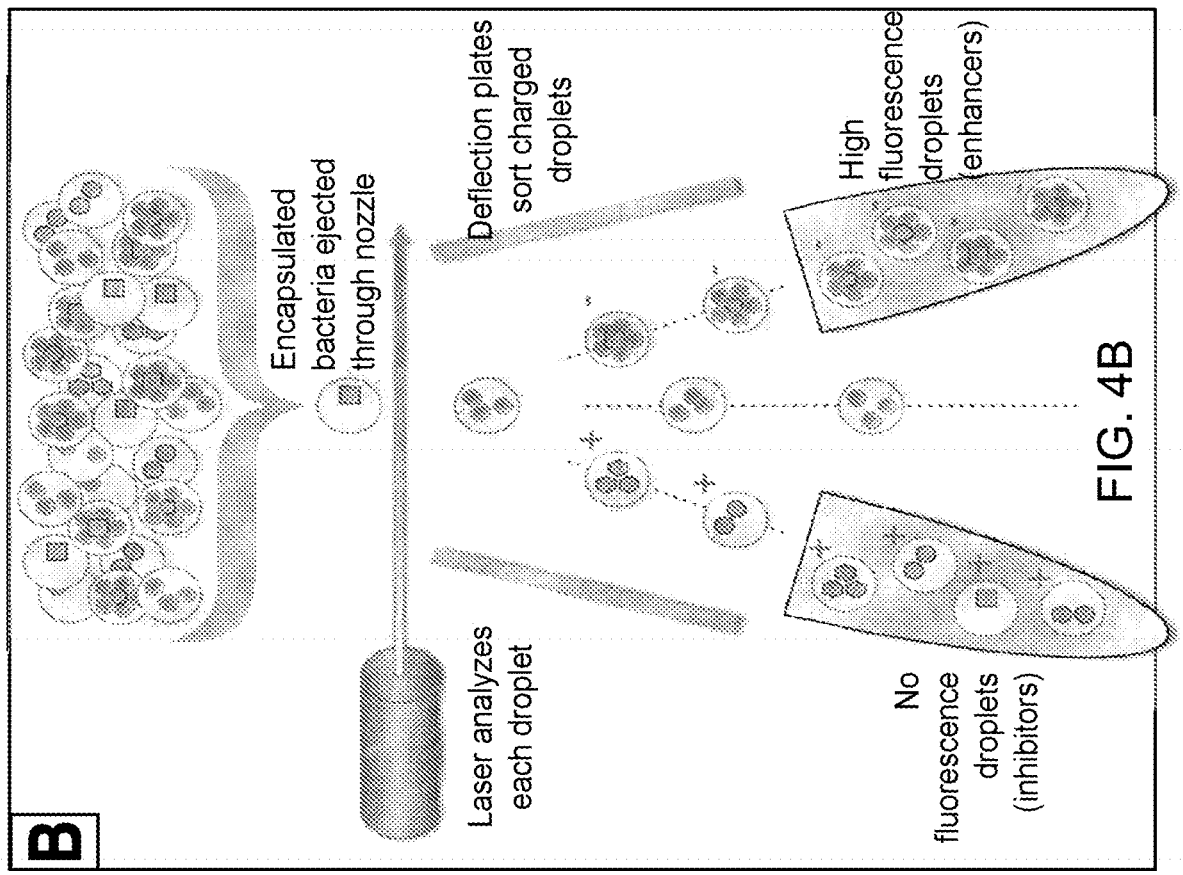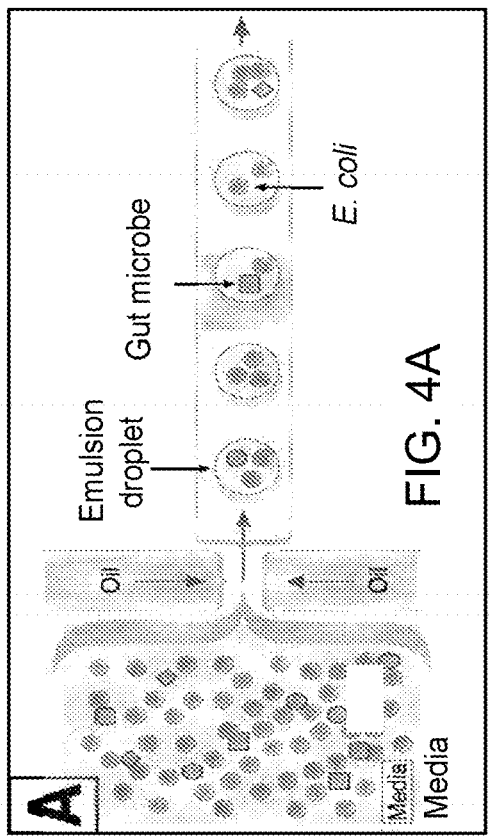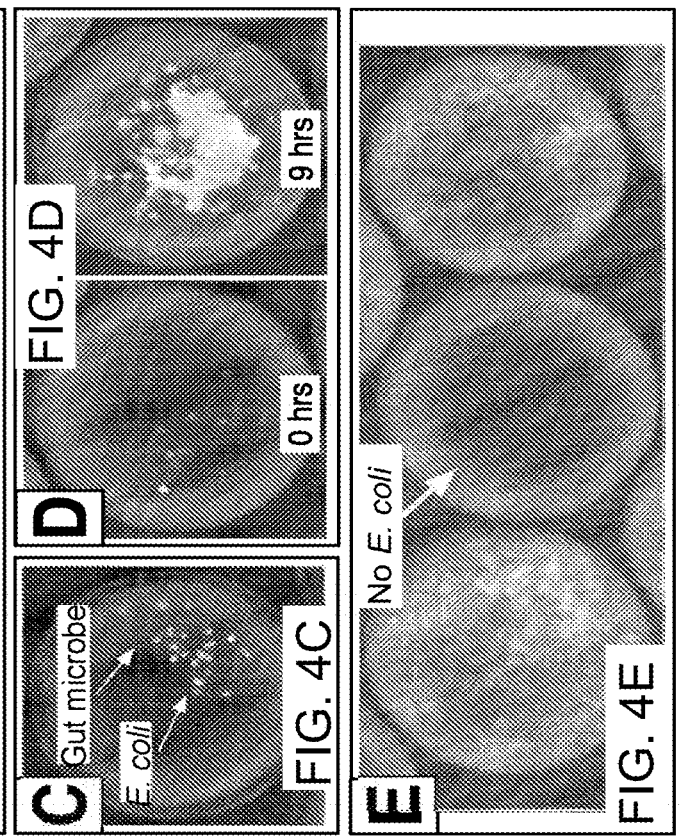

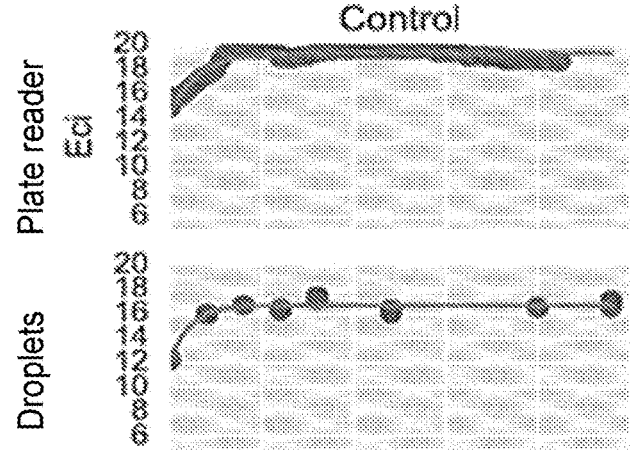 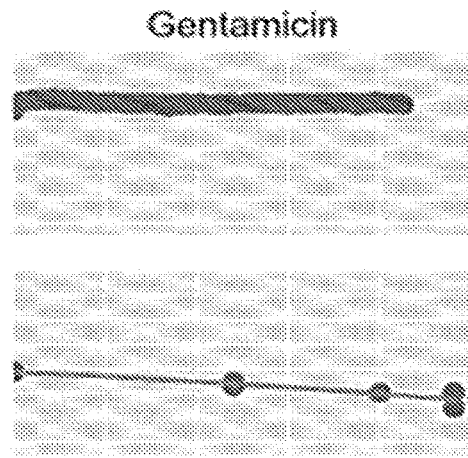
FIG. 7A    FIG. 7B
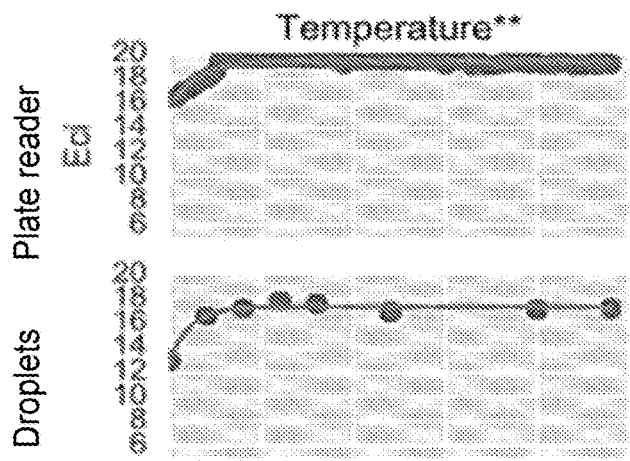 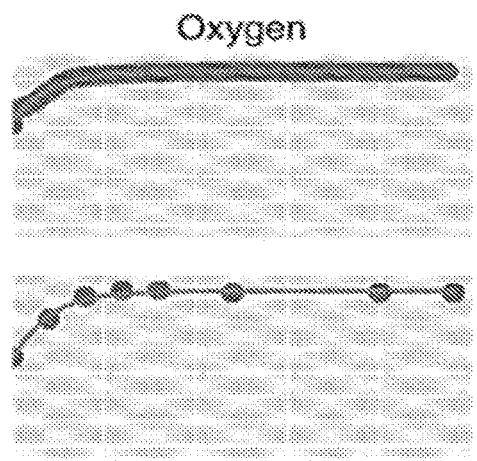
FIG. 7C    FIG. 7D

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: 16s V4 forward primer

<400> SEQUENCE: 1
gtgccagcmg ccgcggtaa                                                19

<210> SEQ ID NO 2
<211> LENGTH: 20
<212> TYPE: DNA
<213> ORGANISM: Artificial Sequence
<220> FEATURE:
<223> OTHER INFORMATION: 16s V4 rRNA reverse primer
```

```
<400> SEQUENCE: 2
ggactachvg ggtwtctaat                                           20
```

COMPOSITIONS AND METHODS FOR MEASURING BACTERIAL GROWTH

CROSS-REFERENCE TO RELATED APPLICATIONS

This application is a U.S. national phase application of International Patent Application No. PCT/US2017/045608, filed on Aug. 4, 2017, which claims the benefit of the filing date of U.S. provisional application No. 62/370,817, filed Aug. 4, 2016, both of which are incorporated herein by reference in their entirety.

SEQUENCE LISTING

The ASCII file, entitled Sequence_Listing.txt, created on Feb. 4, 2019, comprising 679 bytes, submitted concurrently with the filing of this application is incorporated herein by reference. The Sequence Listing submitted herewith is identical to the Sequence Listing forming part of the application.

BACKGROUND OF THE INVENTION

Field of the Invention

The invention disclosed herein relates generally to the fields of microbiology, ecology, and microfluidics. Particularly, the invention disclosed herein provides compositions and methods for isolating bacteria from complex microbial communities and measuring growth rates of the isolated bacteria in a given environmental condition.

Description of Related Art

Microbial communities are essential for ecosystem function, from their role in human health (e.g., the gut and skin microbiome) to their roles in environment (e.g., soil and water microbiomes). Recognition of the importance of these communities leads to the question of how to connect the structure (i.e., what microbes are present) of these microbial communities to their specific role in the ecosystem. In the case of the human microbiome: identification of specific microbes that are essential for human health or disease prevention.

The current standards in the field (e.g., human microbiome field) include surveys of bacteria and fungi present, measuring which bacteria are present in different places on the body, or during different disease states, and, ultimately, trying to correlate different microbes to different conditions. Metagenomic studies, or whole genome surveys of microbial communities, seek to connect specific bacterial genes to a phenotype. Finally, metabolomic techniques are used to associate specific bacterial products to a phenotype. Combining these techniques together would provide for a better picture of how microbial communities affect and respond to the environment around them.

An important piece that is missing is a way to connect bacterial physiology (e.g., the growth) to community structure and function. Growth rate is a fundamental bacterial life history trait. The rate at which a bacterium grows distills many important physiological processes into one variable. Furthermore, the ability to simultaneously measure the growth rates of bacteria isolated from a complex community allows for rapid measurement of the effects of the environment on individual bacterial species. Understanding how individual bacteria of, for example, the gut microbiota respond to diverse environmental factors will enable development of diets or treatments to maintain and promote a healthy gut microbial community. Yet, traditional methods of measuring growth rates for members of the gut microbiota are challenged by the number of unique bacteria inside of one person, and because culturing conditions for most of these bacteria have not yet been described. Problems associated with cultivation hinder traditional methods of measuring growth rates for all the species in the gut. Up to an estimated 80% of microbes from the human gut have not yet been cultivated. Complex culturing conditions, competition in traditional culturing methods, dependence on other bacteria to grow, and low abundances all contribute to the challenge of generating comprehensive culture collections. Any method that comprehensively measures growth rate across the hundreds of species found in the gut microbiota will thus need to address the challenge of isolating uncultivated bacterial taxa.

The complex microbial communities residing inside of our bodies affect human health and disease. Next generation sequencing used to describe community composition has shown abnormal bacterial community profiles associated with disorders such as inflammatory bowel disease, obesity and colorectal cancer. However, composition of bacterial communities based on genotype does not fully predict patient outcomes. For example, metagenomic studies reveal that many microbiota share the same genetic profiles across subjects with different physiological states. The presence of similar genes and pathways suggest an organismal contribution to the host phenotype. Lifestyle and other morphological and boiochemical characteristics of individual bacteria are thus needed to understand how the microbiome contributes to human health.

Two crucial ecological traits to characterize are growth rates of individual species and interactions between populations. Growth rate is a fundamental bacterial life history trait, while interactions between bacteria, such as competition or antagonism, are essential for understanding how a microbial community (e.g., the gut microbial community) functions as a complete ecosystem. However, classical approaches for generating growth curves and co-culturing bacteria are inadequate to handle the complexity of a microbiome. For example, in the gut, each human carries several hundred species of bacteria, and unrelated individuals serve as host to unique strains. Given the trillions of possible bacterial species residing in the billions of people in the world, pure culture connections cannot be created for all human-associated bacterial taxa. Each bacterium would require an order of magnitude more variations of conditions (e.g. media and atmosphere) and consumables (such as plates and tubes) to establish co-culture connections and interactions. Therefore, robust tools are needed that reduce the time and resources needed to isolate and study members of the gut microbiota.

SUMMARY OF THE INVENTION

It is against the above background that this invention provides certain advantages and advancements over the prior art. Specifically, the inventors have found cost-effective and highly efficient high-throughput microfluidics methods for isolating bacteria from complex microbial communities that allow for efficient measurement of growth rates of the isolated bacteria in a given environmental condition.

Although this invention disclosed herein is not limited to specific advantages or functionality, the invention disclosed herein in one aspect provides methods for measuring the growth rate of a bacterial strain from a mixed microbial community, comprising:
(a) isolating a single bacterium by encapsulating the bacterium in an aqueous droplet surrounded by an oil-phase to obtain an encapsulated bacterium;
(b) incubating the encapsulated bacterium under conditions appropriate for growth to obtain a single encapsulated bacterial strain;
(c) extracting DNA from the encapsulated bacterial strain at various time points during incubation;
(d) measuring:
   (i) a quantity of total DNA extracted from each data point using quantitative Polymerase Chain Reaction ("qPCR") via primers that target a variable region within a conserved gene sequence; and
   (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

Another aspect of the disclosure provides methods for assessing the potential for a bacterial strain from a mixed microbial community to develop resistance to an antibiotic drug, comprising:
(a) isolating a single bacterium by encapsulating the bacterium in an aqueous droplet surrounded by an oil-phase to obtain an encapsulated bacterium;
(b) incubating the encapsulated bacterium in the presence of an antibiotic drug, under conditions appropriate for growth to obtain a single encapsulated bacterial strain;
(c) extracting DNA from the encapsulated bacterial strain at various time points during incubation;
(d) measuring:
   (i) a quantity of total DNA extracted from each data point using quantitative Polymerase Chain Reaction ("qPCR") via primers that target a variable region within a conserved gene sequence; and
   (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

Another aspect of the disclosure provides methods for characterizing the microflora in a patient's gut, comprising:
(a) isolating each bacterium within a patient's stool sample by individually encapsulating the bacterium in an aqueous droplet surrounded by an oil-phase to obtain individually encapsulated bacteria;
(b) incubating each encapsulated bacterium under conditions appropriate for growth to obtain encapsulated bacterial strains;
(c) extracting DNA from each encapsulated bacterial strain at various time points during incubation;
(d) measuring:
   (i) a quantity of total DNA extracted from each data point using quantitative Polymerase Chain Reaction ("qPCR") via primers that target a variable region within a conserved gene sequence; and
   (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

Another aspect of the disclosure provides methods for identifying bacteria from a mixed microbial community which have an inhibitory effect on a target bacteria, comprising:
(a) adding a fluorescent-labeled target bacterial strain to a suspension containing a mixed microbial community;
(b) isolating a bacterial cell from a mixed microbial community and a fluorescent-labeled target bacterial cell together by encapsulating the two bacterial cells in an aqueous droplet surrounded by an oil-phase to obtain an encapsulated co-culture;
(b) incubating the encapsulated co-culture under conditions appropriate for growth to stationary phase;
(c) sorting the co-cultured droplets using Fluorescence Activated Cell Sorting (FACS); and
(d) detecting co-cultured droplets exhibiting bacterial growth of a mixed community bacterial strain, but lacking fluorescence.

Another aspect of the disclosure provides libraries of bacteria which inhibit growth of a target bacterium, generated according to the methods of the disclosure.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of this invention can be best understood when read in conjunction with the following drawings.

(FIG. 1A); the relative abundance and absolute DNA amounts generated for each time point; (FIGS. 1B-1C); growth curve for each individual bacterium (FIG. 1D), generated by combining the relative abundance with the total DNA quantity, respectively.

FIGS. 4A-4E are images and schematics showing the encapsulation of clonal populations of gut bacterial with fluorescently labeled *E. coli* in droplets of media in accordance with one embodiment of the present disclosure. FIG. 4A shows encapsulation of clonal populations of gut bacteria with fluorescently labeled *E. coli* in droplets of media surrounded by oil; FIG. 4B shows Fluorescence Activate Cell Sorting (FACS) of the droplets; FIG. 4C shows *E. coli* labeled with GFP and a gut microbe stained with DAPI encapsulated in the same droplet; FIG. 4D shows growth of *E. coli* in a droplet for 9 hours (growth dynamics of *E. coli* are normal in a droplet); FIG. 4E shows after 24 hour incubation of *E. coli* and a random gut bacteria, some droplets (arrow) revealed no growth of *E. coli*, but instead the growth of another non-fluorescent bacteria (seen in phase contrast, data not shown).

FIG. 6A shows the total amount of DNA identified from running qPCR on 16S V4 rRNA at each time point; FIG. 6B shows the relative abundance of each bacterial population at each time point, which is generated from sequencing of 16S V4 rRNA with Next Gen Sequencing; FIG. 6C shows growth curves generated for each of the bacterial populations; solid lines represent fit growth curves, and points represent the cell numbers (qpcr* relative abundance).

FIGS. 7A-7D show growth of *E. coli* under different conditions. FIG. 7A shows the control condition, which is anaerobic at 37° C. in modified Gifu Anaerobic Medium; FIG. 7B shows growth under control conditions, with the addition of the antibiotic gentamicin; FIG. 7C shows growth under anaerobic conditions at 39° C.; and FIG. 7D shows growth under aerobic conditions (in the presence of oxygen). The top row shows *E. coli* growth measured in the plate reader, while the bottom row shows *E. coli* growth measured from the mixed community of *Escherichia coli, Bacteroides fragilis, Bifidobacterium longum*, and *Enterococcus faecalis* in droplets.

DETAILED DESCRIPTION OF THE INVENTION

Figure 1A:
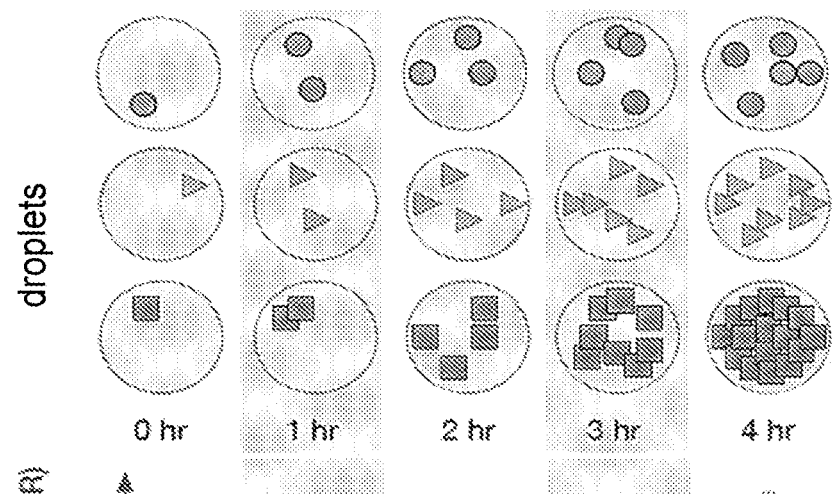
FIGS. 1A-1D are graphs and images showing individual bacterium encapsulated and incubated in droplets.
Figure 1B:
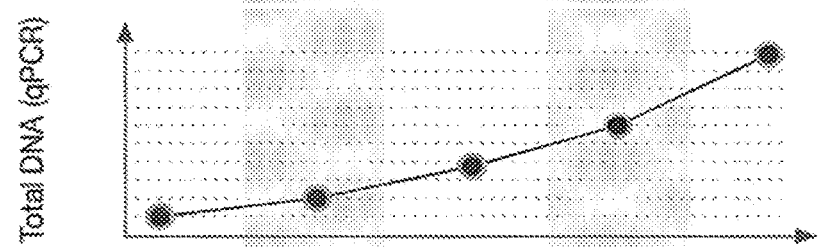
Figure 1C:
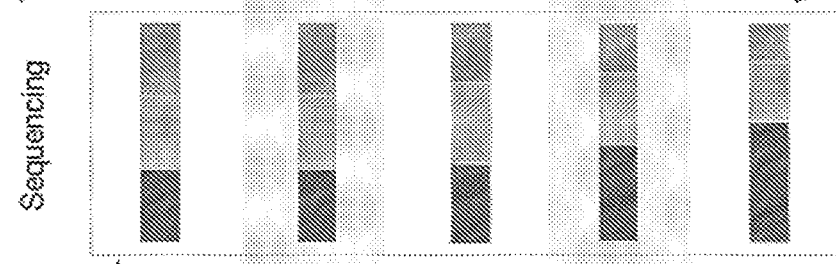
Figure 1D:
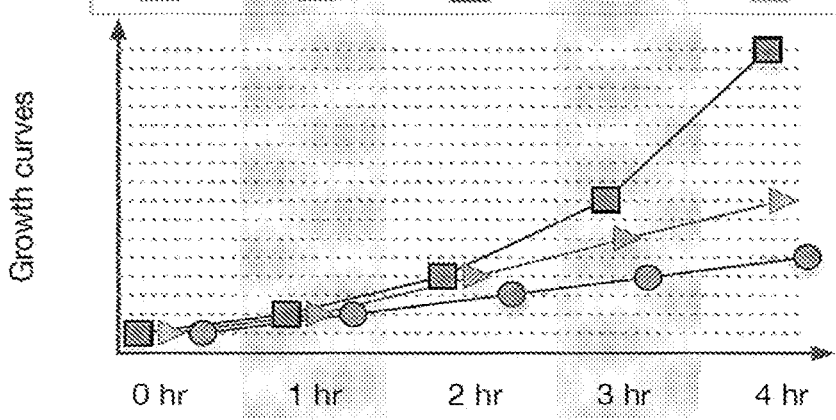
Figure 2:
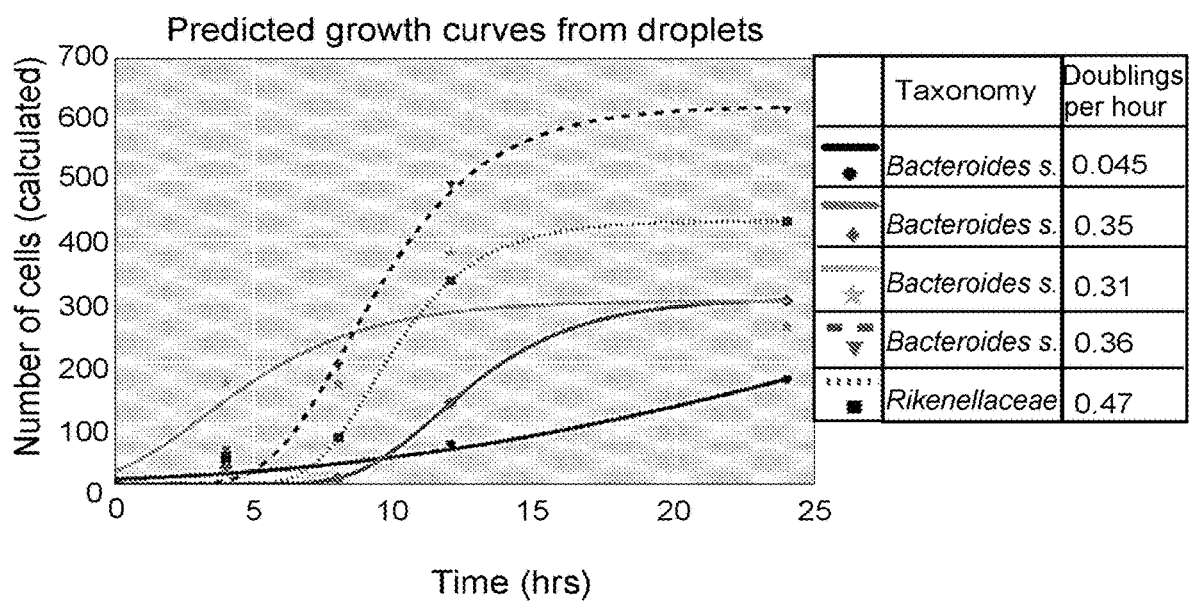
FIG. 2 shows growth curves fit with the Gompertz function and individual taxa from the Bacterioides genera and Rikenellaceae family in accordance with one embodiment of the present disclosure.
Figure 3:
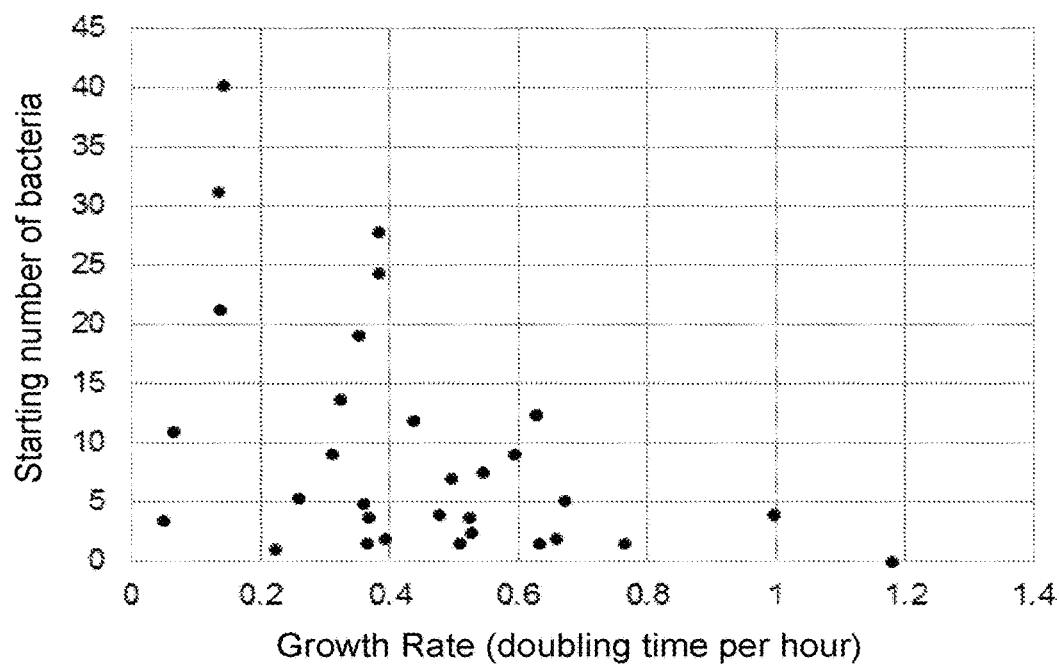
FIG. 3 is a graph showing a correlation between the growth rate of a bacteria and its starting abundance from the fecal inoculum in accordance with one embodiment of the present disclosure. (p-value=0.016)

All publications, patents and patent applications cited herein are hereby expressly incorporated by reference for all purposes.

Before describing this invention in detail, a number of terms are defined. As used herein, the singular forms "a", "an", and "the" include plural referents unless the context clearly dictates otherwise. For example, reference to "an element" means at least one element and can include more than one element.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the terms "reduced", "reduction", "increase", "increases", "increased", "greater", 'higher', and "lower" are utilized herein to represent comparisons, values, measurements, or other representations to a stated reference or control.

For the purposes of describing and defining this invention it is noted that the term "about" is used to provide flexibility to a numerical range endpoint by providing that a given value may be "slightly above" or "slightly below" the endpoint without affecting the desired result.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

Microfluidics has made impressive progress isolating uncultivated bacteria. Recent attempts to cultivate bacteria from complex environments have relied on microfluidic devices that scale down the amount of reagents needed to culture and scale up the amount of organisms able to be isolated at one time. These microfluidic devices use complex diffusion chambers, in the case of the iChip, which captures bacteria in chambers then exposes them to complex environmental conditions. The iChip is thus able to identify novel species that cannot grow in current laboratory media. Similarly, another device, the SlipChip, confines individual bacteria into microscopic wells on a chip, and the colonies trapped in these wells are able to be propagated for isolation. Both of these microfluidic devices were specifically designed for isolation of bacteria, but neither is well-equipped to perform high-throughput phenotypic characterization of bacterial isolates.

The diversity of the gut microbiota and other complex microbial communities is maintained in part by interactions between bacteria. Antagonism between populations is one type of interaction that contributes to the diversity, and these interactions are often mediated by small molecules including antibiotic compounds. Recently, there has been renewed interest in mining the gut microbiota for yet-undiscovered molecules that could have known antimicrobial activity. Among the uncharacterized portion of the gut microbiota there may be useful treatments to prevent the colonization of pathogens. To identify interactions between two species of bacteria, microbiologists traditionally co-culture bacteria, growing them together, and looking for inhibition. To look at the interactions between members of the genera *Vibrio*, over 35,000 possible interactions were previously screened to understand the population structure of microbes in the ocean. Over 30,000 isolates from the gut microbiota were previously screened for antimicrobial activity against the pathogen *Clostridium difficile* and a novel two-component antimicrobial peptide was identified. Other attempts to identify probiotic candidates have included computationally predicting the presence of over 3,000 small-molecule biosynthetic gene clusters in the human gut microbiome. The presence, structure, and antibacterial activity was subsequently verified for one of the compounds. Culturing two or more bacterial species together is the primary way of identifying interactions between species. An individual gut microbiota contains as many as 1,000 different species; therefore, to test all possible pairwise interactions (499,500) would be burdensome, requiring over 5,000 96-well plates for culturing alone.

There is thus a need in this art to develop approaches that both isolate bacteria and allow high-throughput phenotypic characterization, as well as high-throughput identification of antagonistic and other interactions between bacterial members of a microbial community.

In general, the disclosed materials, methods, and apparatus provide improvements in methods for isolating bacteria from complex microbial communities that are cost-effective and highly efficient. Specifically, the inventors have founds that use of high-throughput microfluidics methods of the disclosure allow for efficient measurement of growth rates of the isolated bacteria in a given environmental condition.

Thus, one aspect of the disclosure provides methods for measuring the growth rate of a bacterial strain from a mixed microbial community, comprising:
(a) isolating a single bacterium by encapsulating the bacterium in an aqueous droplet surrounded by an oil-phase to obtain an encapsulated bacterium;
(b) incubating the encapsulated bacterium under conditions appropriate for growth to obtain a single encapsulated bacterial strain;
(c) extracting DNA from the encapsulated bacterial strain at various time points during incubation;
(d) measuring:
  (i) a quantity of total DNA extracted from each data point using quantitative Polymerase Chain Reaction ("qPCR") via primers that target a variable region within a conserved gene sequence; and
  (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

Another aspect of the disclosure provides methods for assessing the potential for a bacterial strain from a mixed microbial community to develop resistance to an antibiotic drug, comprising:
(a) isolating a single bacterium by encapsulating the bacterium in an aqueous droplet surrounded by an oil-phase to obtain an encapsulated bacterium;
(b) incubating the encapsulated bacterium in the presence of an antibiotic drug, under conditions appropriate for growth to obtain a single encapsulated bacterial strain;
(c) extracting DNA from the encapsulated bacterial strain at various time points during incubation;
(d) measuring:
  (i) a quantity of total DNA extracted from each data point using quantitative Polymerase Chain Reaction ("qPCR") via primers that target a variable region within a conserved gene sequence; and
  (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

In one embodiment of the methods as otherwise described herein, the antibiotic drug is gentamicin. In one embodiment, gentamicin is present at a concentration of 50 µg/mL, or about 10 µg/mL to about 100 µg/mL, or about 10 µg/mL to about 60 µg/mL, or about 10 µg/mL to about 50 µg/mL, or about 25 µg/mL to about 100 µg/mL, or about 25 µg/mL to about 60 µg/mL, or about 25 µg/mL to about 50 µg/mL, or about 30 µg/mL to about 70 µg/mL, of about 40 µg/mL to about 60 µg/mL, or about 45 µg/mL to about 55 µg/mL.

Another aspect of the disclosure provides methods for characterizing the microflora in a patient's gut, comprising:
(a) isolating each bacterium within a patient's stool sample by individually encapsulating the bacterium in an aqueous droplet surrounded by an oil-phase to obtain individually encapsulated bacteria;
(b) incubating each encapsulated bacterium under conditions appropriate for growth to obtain encapsulated bacterial strains;
(c) extracting DNA from each encapsulated bacterial strain at various time points during incubation;
(d) measuring:
  (i) a quantity of total DNA extracted from each data point using quantitative Polymerase Chain Reaction ("qPCR") via primers that target a variable region within a conserved gene sequence; and
  (ii) a relative abundance of the encapsulated bacterial strain through sequencing of the same variable region within a conserved gene sequence as in (i) using the same primers as in (i); and
(e) generating a growth curve based on the measurements obtained in (d) at each time point.

Another aspect of the disclosure provides methods for identifying bacteria from a mixed microbial community which have an inhibitory effect on a target bacteria, comprising:
(a) adding a fluorescent-labeled target bacterial strain to a suspension containing a mixed microbial community;
(b) isolating a bacterial cell from a mixed microbial community and a fluorescent-labeled target bacterial cell together by encapsulating the two bacterial cells in an aqueous droplet surrounded by an oil-phase to obtain an encapsulated co-culture;
(b) incubating the encapsulated co-culture under conditions appropriate for growth to stationary phase;
(c) sorting the co-cultured droplets using Fluorescence Activated Cell Sorting (FACS); and
(d) detecting co-cultured droplets exhibiting bacterial growth of a mixed community bacterial strain, but lacking fluorescence.

In one embodiment, the method further comprises sequencing the bacterial strain within each co-cultured droplet exhibiting bacterial growth, but lacking fluorescence, using quantitative Polymerase Chain Reaction ("qPCR") via primers that target a variable region within a conserved gene sequence.

In one embodiment of the methods as otherwise described herein, the isolation of the bacterium via encapsulation is random.

In one embodiment of the methods as otherwise described herein, the encapsulated bacterium is incubated under anaerobic conditions.

In one embodiment of the methods as otherwise described herein, the aqueous droplet encapsulating the bacterium comprises nutrient-rich culture media. In some embodiments, the nutrient-rich culture media comprises Brain Heart Infused (BHI) medium, Gifu Anaerobic Medium (GAM) or modified Gifu Anaerobic Medium (mGAM). In some embodiments, the nutrient-rich culture media is modified to include one or more of the following: change in pH or change in salt (NaCl) concentration.

In one embodiment of the methods as otherwise described herein, the aqueous droplet encapsulating the bacterium comprises defined media.

In some embodiments of the methods as otherwise described herein, the aqueous droplets encapsulating bacteria are incubated at 37° C. In some embodiments of the methods as otherwise described herein, the aqueous droplets encapsulating bacteria are incubated at 39° C. In some embodiments of the methods as otherwise described herein, the aqueous droplets encapsulating bacteria are incubated at a temperature of about 30° C. to about 45° C., or about 35° C. to about 42° C., or about 36° C. to about 40° C., or about 37° C. to about 39° C.

In one embodiment of the methods as otherwise described herein, the primers target a variable region within conserved gene sequence 16s ribosomal RNA ("rRNA"). In one embodiment of the methods as otherwise described herein, the primers comprise GTGCCAGCMGCCGCGGTAA (SEQ ID NO:1), and GGACTACHVGGGTWTCTAAT (SEQ ID NO:2).

In one embodiment of the methods as otherwise described herein, the growth curve is generated by multiplying the relative abundance sequencing data obtained for each time point by the quantitative qPCR data obtained for each time point, respectively.

In one embodiment of the methods as otherwise described herein, the primers target a variable region within conserved gene sequence 16s ribosomal RNA ("rRNA"). In one embodiment of the methods as otherwise described herein, the primers comprise GTGCCAGCMGCCGCGGTAA (SEQ ID NO:1), and GGACTACHVGGGTWTCTAAT (SEQ ID NO:2).

Measuring Growth Rates of Bacterial Species within Complex Microbial Communities The present disclosure provides, in part, methods to measure properties such as antibiotic susceptibility profiles, drug breakdown on the human gut, and response of bacterial communities to the addition of foreign compounds, for hundreds of species in a single day. The human gut microbiome is a complex ecosystem affecting human health and disease. Due to the amount and variation of the bacterial populations that reside inside our gastrointestinal tract (e.g., the gut microbiota), however, ecological traits of individual bacteria remain uncharacterized. Two traits essential to understanding the functioning microbial community are: growth rates of individual bacterial populations and the interactions between bacterial populations.

In some aspects, the present disclosure provides a method to measure the growth rate of bacteria from mixed communities in a high-throughput manner. One of skill in the art recognizes that the standard method for growth rate is an essential variable to measure because it encompasses so many aspects of bacterial physiology. The ability to measure growth rate of bacteria from a community provides a better picture of an individual microbe's role in the larger community. High-throughput droplet microfluidic techniques are used herein to measure the growth of individual members of the gut microbiota and identify interactions between species. Thus, one aspect of the present disclosure provides droplet microfluidic techniques to isolate an individual bacterium from a complex environment (i.e., as one non-limiting example, from the human gut microbiota). In some embodiments of the present disclosure, once the individual bacteria are isolated, next generation DNA sequencing combined with quantitative Polymerase Chain Reaction (qPCR) are used to measure the growth rate of bacterial populations isolated within the droplets. These novel techniques make previously uncultivated members of the gut microbiota amenable for experimentation and increase understanding of how individual members of the gut microbiota grow, interact, and contribute the gut microbial community and, subsequently, to the health of the host.

In some embodiments, the present disclosure provides a method for rapidly isolating and measuring the growth rate of members of a bacterial environmental community comprising, consisting of, or consisting essentially of encapsulating individual bacteria in droplets using a droplet chip to produce aqueous droplets of a chosen growth media surrounded by an oil-phase; culturing the anaerobic bacteria in an anaerobic chamber; incubating the encapsulated droplets at an appropriate temperature; extracting DNA from the droplets; measuring both relative abundances of different taxa and the amount of DNA present using primers (such as the 16S V4 primers); and computing the absolute growth.

In some embodiments, this technique generates about 10,000 to about 100,000 droplets per minute, for example, about 10,000 to about 80,000 droplets per minute, or about 10,000 to about 60,000 droplets per minute, or about 30,000 to about 80,000 droplets per minute, or about 30,000 to about 70,000 droplets per minute, or about 30,000 to about 60,000 droplets per minute, or about 30,000 to about 50,000 droplets per minute, or about 40,000 to about 80,000 droplets per minute, or about 40,000 to about 70,000 droplets per minute, or about 40,000 to about 60,000 droplets per minute, or about 45,000 to about 55,000 droplets per minute, or about 48,000 to about 52,000 droplets per minute, or about 40,000 droplets per minute, about 50,000 droplets per minute, or about 55,000 droplets per minute.

The generated droplets capture individual bacteria within the droplets. The size and scale of the droplets makes individually encapsulating a single bacterium feasible. Thus, in some embodiments, the individual droplets may average from about 10 μm to about 1 mm in diameter, for example, about 10 μm to about 750 μm, or about 10 μm to about 500 μm, or about 10 μm to about 250 μm, or about 10 μm to about 200 μm, or about 10 μm to about 150 μm, or about 10 μm to about 100 μm, or about 50 μm to about 1 mm, or about 50 μm to about 750 μm, or about 50 μm to about 500 μm, or about 50 μm to about 250 μm, or about 50 μm to about 200 μm, or about 50 μm to about 150 μm, or about 50 μm to about 100 μm, or about 100 μm to about 1 mm, or about 100 μm to about 750 μm, or about 100 μm to about 500 μm, or about 100 μm to about 250 μm, or about 100 μm to about 200 μm, or about 75 μm to about 125 μm, or about 80 μm to about 120 μm, or about 90 μm to about 110 μm, or even about 100 μm in diameter.

Because the random encapsulation of bacteria in a droplet follows the Poisson distribution, when about 30% of droplets have bacteria in them, over about 90% of those droplets have clonal populations of bacteria. The large amount of empty droplets is rapidly overcome by the total number of droplets produced. In some embodiment of this disclosure, a bacterium is individually encapsulated in a droplet, using a high-throughput method. Droplets may be generated by any method known in the art, such as, without limitation, a droplet chip, centrifugation, mechanical shaking of two immiscible liquids (such as water and oil), microfluidic chip, etc. In one embodiment, droplets are generated using a 6-junction droplet chip available from Dolomite® microfluidics. The droplet chip produces aqueous droplets of a chosen growth media surrounded by an oil-phase (i.e., water-in-oil droplets). Any suitable hydrophobic material having suitable viscosity and/or interfacial tension may be used for the oil phase. Hydrophobic materials suitable for use in the methods of the disclosure include, but are not limited to, mineral oil, silicon oil, perfluorinated oil, and fluoro-carbon oil (such as one available from Biorad®.)

In some embodiments, the entire microfluidic setup is placed within an anaerobic (e.g., oxygen-free) chamber to culture the bacteria. In some embodiments, the bacteria are encapsulated within and incubated in an aqueous droplet containing nutrient-rich culture media. One of skill in the art would immediately recognize that this encompasses any suitable kind of media classified as nutrient-rich, including, but not limited to: Brain Heart Infused (BHI) medium, Gifu Anaerobic Medium (GAM), and modified Gifu Anaerobic Medium (mGAM). In some embodiments, the bacteria are encapsulated within, as well as incubated in, an aqueous droplet containing defined media. One of skill in the art would immediately recognize that this encompasses any suitable media classified as defined media, including media with known and defined sources of carbon, nitrogen, and salt (NaCl) which is necessary for growth of certain type of bacteria. In some embodiments, the encapsulated bacteria are grown under a range of conditions, including changes to pH, temperature, and salt content.

In some embodiments, growth rates of the bacteria isolated in droplets are characterized through next generation DNA sequencing combined with quantitative PCR (qPCR). In some embodiments, once bacteria are encapsulated, the droplets are incubated at an appropriate temperature (e.g., 37° C.). In some embodiments, DNA is extracted from the incubating droplets at set time points (e.g., at 60 minutes, or at 6 hours, or at 12 hours, or at 22 hours, or at 24 hours or later).

Two different measurements are performed on the extracted DNA. In some embodiments, both relative abundances of different taxa and the amount of DNA present are measured using suitable primers. In some embodiment, the primers include the 16s rRNA primers. In some embodiments, the primers include the 16s V4 rRNA primers: forward primer GTGCCAGCMGCCGCGGTAA (SEQ ID NO:1) and reverse primer GGACTACHVG GGTWTCTAAT (SEQ ID NO:2).

In some embodiments, absolute growth is determined by multiplying the quantitative qPCR data and the relative abundances from sequencing, and used to create growth curve measurements. In some embodiments, growth rates are further determined by fitting a Gompertz® growth model. In this way the growth rates of individual bacteria can be measured directly from an environmental community.

Identifying and Assessing Interactions Between Bacterial Species

The human gut contains over one-thousand different types of bacteria and upwards of 500,000 possible pair-wise interactions. Accordingly, a high-throughput screen is necessary to comprehensively test interactions between members of the gut microbiota. In some embodiments, microfluidics is used to co-culture clonal populations of bacteria in droplets. In some embodiments, combining microfluidics with flow cytometry allows for rapid screening of co-cultured bacteria for antagonistic interactions between species. In some embodiments, this screen targets a pathogenic *Escherichia coli* (*E. coli*) with direct relevance to developing probiotic treatments for disease.

Microfluidics scales down both time and reagents needed for co-culture reactions, providing a feasible technique to identify and test interactions among the gut microbiota. In some embodiments, to rapidly co-culture members of the gut microbiota, bacteria from the gut are encapsulated in droplets with a target bacteria (e.g., *E. coli*, or a pathogenic bacteria, such as enterohemorrhagic *E. coli* (EHEC)). Simultaneously loading a random member of the gut microbiota into a droplet (as described above) with fluorescently labelled *E. coli* (illustrated in FIG. 4A) create hundreds of thousands of co-cultures at one time. In some embodiments, the randomly assembled co-cultures incubate for sufficient time for *E. coli* to reach stationary phase due to limited space and nutrients inside of the droplet (for example, for about 24 hours, or about 20 to 28 hours, or about 20 to about 48 hours). Most bacteria-produced antibiotics are synthesized in late exponential and stationary phase making this a reasonable time for co-culturing the two populations. In some embodiments, after incubating, the co-cultures are sorted based on the fluorescence of *E. coli* (FIG. 4B.) In some embodiments, using Fluorescence Activated Cell Sorting (FACS) allows for sorting millions of droplets per hour. Absence of fluorescence indicates that *E. coli* was unable to grow in the presence of the random member of the gut microbiota, implying the presence of antagonism between the two bacteria. In some embodiments, a comprehensive library of inhibitors of *E. coli* is then generated by isolating non-fluorescent droplets. This approach screens the entire gut microbiota for antagonism against *E. coli*, identifying potential probiotic therapies.

Effect of Culture Conditions on Interactions.

In some embodiments, the conditions under which to co-culture bacteria are systematically varied to characterize and prioritize interactions identified in the screen. In some embodiments, changing the culture conditions of the interaction screen reveal interactions that are sensitive to the environment, compared to those that are not. For example, an interaction that exists between two bacteria under only one nutritional condition may be due to competition over that one resource. Conversely, an interaction present across multiple nutritional conditions indicates that this is a direct antagonistic interaction between the two bacteria.

*E. coli* grows normally in droplets (FIG. 4D) and when co-cultured in droplets, exhibits antagonism. In some embodiments, after incubating droplets with fluorescently-labeled *E. coli* and a random member of the gut microbiota (FIG. 4C), some droplets contain bacteria and were not fluorescent (FIG. 4E, arrow, phase contrast data not shown.) This result suggests that antagonism between bacteria in microfluidic droplets may be detected. In some embodiments, this screen allows for identification and recovery of specific bacteria or bacterial products that antagonize EHEC. In some embodiments, other *E. coli* strains inhibit the growth of EHEC within droplets. This is due to the tenet proposed by Charles Darwin that there is more competition between closely related species because similar species compete for the same resources. Indeed, it has recently been shown that nutrient competition between commensal *E. coli* and EHEC confers a resistance to EHEC infection in mice. The ability of a commensal species to use the same nutrients more efficiently than EHEC would prevent EHEC from growing in the droplets. In some embodiments, screening provides the ability to identify both commensal strains of *E. coli* that prevent the growth of EHEC and other enteric pathogens due to competition, as well as unrelated bacteria that inhibit EHEC or other enteric pathogens by other mechanisms. Based on studies in the marine bacteria *Vibrio*, antagonistic interactions occurred between populations of greater phylogenetic distance, due to the presence of an antibiotic and closely related populations which harbored the same resistance genes that less related populations did not. In the same way, screening non-pathogenic bacteria against the gut microbiota allows for identification of important interactions between the non-disease causing members of our microbiota. These interactions are important in maintaining the health of the gut microbial community and, subsequently, of the human host. Screening enables identification of multiple types of antagonistic interactions, including preventing growth through a direct mechanism of inhibition, as well as interactions mediated by small molecules, and other mechanisms, including competition. These same screening techniques can be applied to screen for antagonism within the entire gut microbiota at one time against enterohemorrhagic *E. coli* (EHEC) and other enteric pathogens. This provides a rapid way to identify candidates for probiotics for disease prevention.

The invention is further described in the following examples, which do not limit the scope of the invention described in the claims.

EXAMPLES

Figure 5:
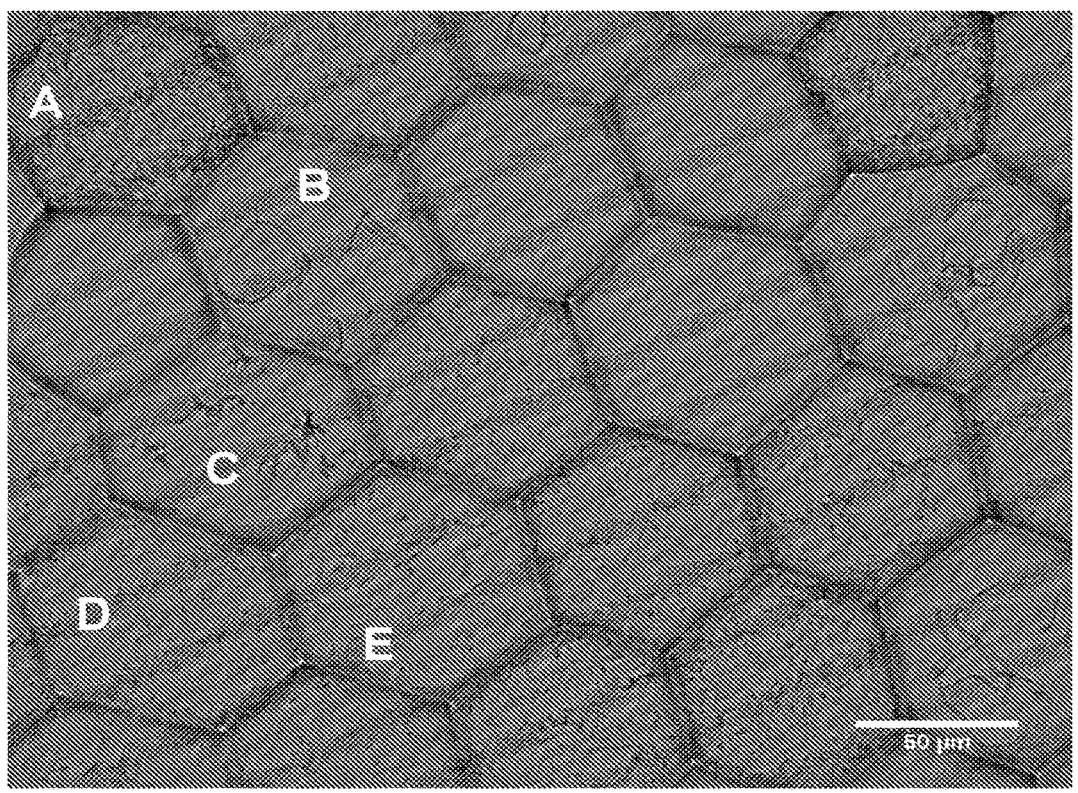
FIG. 5 is an image showing the separate encapsulation of five (5) facultative anaerobic bacteria isolated from the human gut: *Escherichia coli, Streptococcus agalactiae, Enterococcus faecalis, Enterobacter cloacae*, and *Staphylococcus haemolyticus*, each of which shows a distinct bacterial morphology within droplets labelled A-E.

Example 1: Isolation and Growth of Bacteria in Individual Droplets (A) Human stool samples were obtained and used to isolate individual bacterium within the human gut: *Escherichia coli, Streptococcus agalactiae, Enterococcus faecalis, Enterobacter cloacae, Staphylococcus haemolyticus*. These five facultative anaerobic bacteria were then encapsulated in aqueous droplets using a 6-junction droplet chip (Dolomite® microfluidics). The droplet chip produces aqueous droplets of a chosen growth media (such as Brain Heart Infusion (BHI) medium used in this example), which is surrounded by an oil-phase (fluoro-carbon oil, Biorad®). The droplets were incubated in growth media at 37° C., under aerobic conditions for ~12 hours. After incubation, the droplets demonstrate five distinct bacterial morphologies within droplets labelled A-E. (FIG. 5). These results also demonstrate the ability to isolate bacteria from a mixed community into individual droplets. (FIG. 5).

Figure 6A:
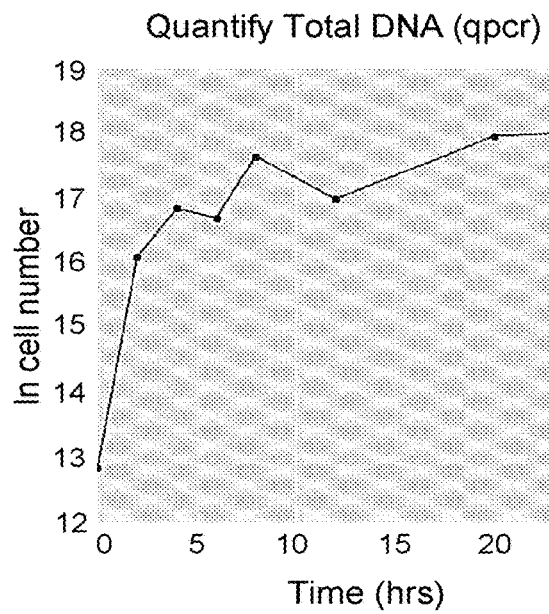
FIGS. 6A-6C are graphs of a mixed community of *Eschericia coli, Bacteroides fragilis, Bifidobacterium longum*, and *Enterococcus faecalis*, isolated and grown in droplets according to the disclosure.
Figure 6B:
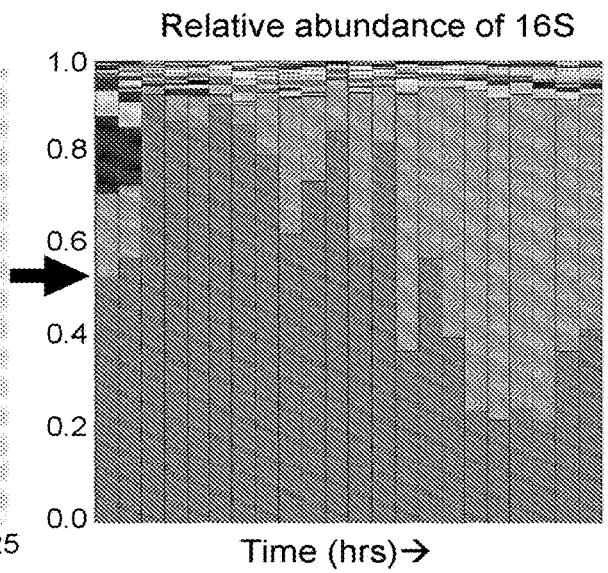
Figure 6C:
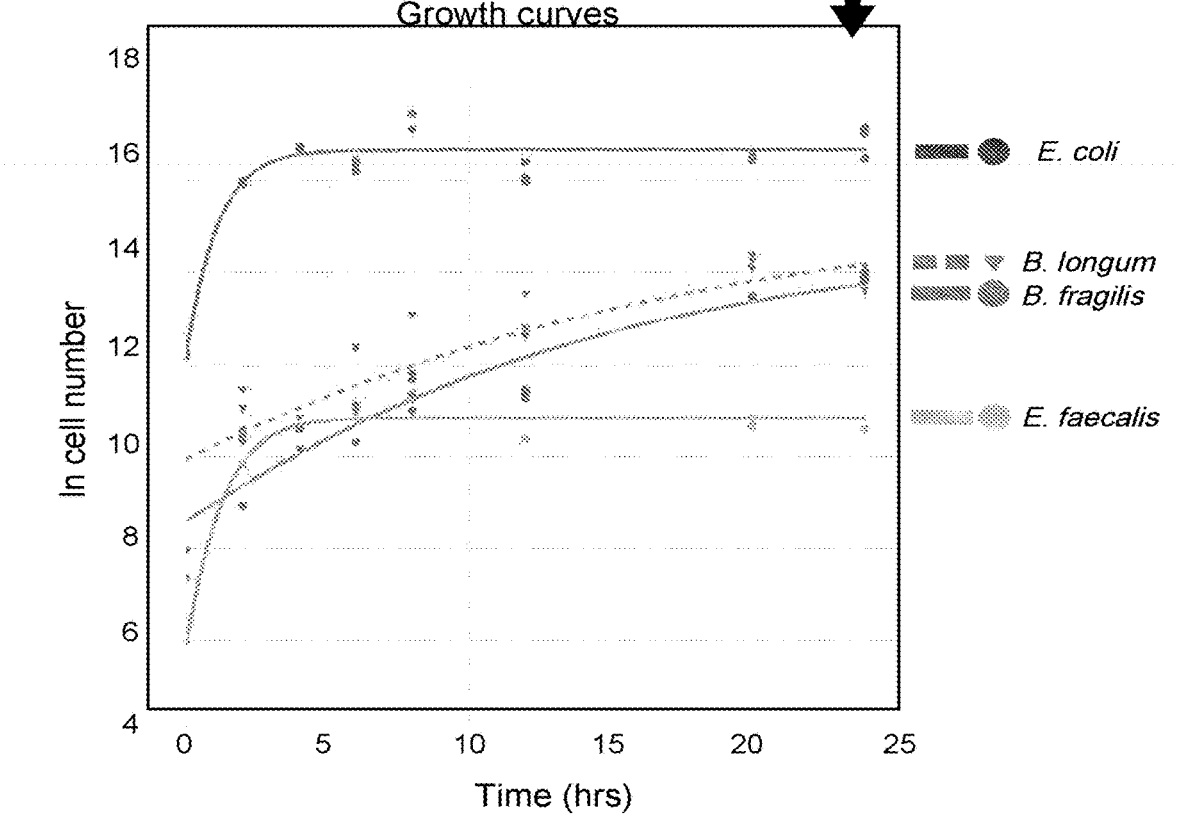

(B) A sample of a mixed community of four bacteria native to the human gut was generated. The four bacteria: *Escherichia coli, Bacteroides fragilis, Bifidobacterium longum*, and *Enterococcus faecalis*, represent the four most dominant phyla in the gut: Proteobacteria, Bacteroidetes, Actinobacteria, and Firmicutes, respectively. Droplets were generated using a 6-junction droplet chip (Dolomite® microfluidics), flowing Gifu Anaerobic Media with the addition of vitamin K and Hemin (modified Gifu) through the oil (fluoro-carbon oil, Biorad®). The media contained the mixed community of the four bacteria described, diluted to isolate only one bacterium per droplet. The droplets were incubated anaerobically at 37° C. for 24 hours. Samples were taken every two hours for 12 hours, and then at 22 and 24 hours. DNA was extracted using a standard extraction kit, and qPCR was used to quantify the total amount of DNA by measuring 16S V4 rRNA at each time point, using the 16S V4 rRNA primers (GTGCC AGCMG CCGCG GTAA (SEQ ID NO: 1) and GGACT ACHVG GGTWT CTAAT (SEQ ID NO: 2)). (FIG. 6A). The 16S V4 rRNA gene was simultaneously sequenced with Next Gen Sequencing (Illumina MiSeq) to obtain the relative abundance of each bacterial taxa. (FIG. 6B). Absolute measurements for each taxa were generated by multiplying the qPCR result at each time point by the relative abundance of each taxa at each time point, respectively. (FIG. 6C). The growth rate curves were further determined by fitting a Gompertz® growth modelo the absolute measurements. (FIG. 6C). In this way the growth rates of individual bacteria can be measured directly from an environmental community without prior isolation. The results in the relative abundance plot (FIG. 6B) highlights what is unique and important about using the disclosed method: towards the later time points (the right hand side of the plot) it appears that the community is dominated by the light gray and dark gray bars, while the black bars, which are present in the earlier time points appear to disappear at the scale represented. (FIG. 6B). However, when the relative abundances are multiplied by the total amount of DNA (FIG. 6A), clear growth curves are discernable for each taxa. (FIG. 6C). The apparent "loss" of the black and other taxa in (FIG. 6B) is explained by the lower growth rates from *B. fragilis* and *B. longum*, due to the higher growth rates of *E. coli* and *E. faecalis*, which appear to dominate the relative abundance plots at later time points. This illustrates how relative abundance alone does not capture the dynamics of microbial communities, and that by isolating bacteria in droplets and measuring their growth rates, the community dynamics are captured. (FIGS. 6A-6C).

Example 2: Growth Rates of Isolated Bacteria Under Different Conditions

The bacterial community from Example 1(B) was further tested against the following four conditions. A) control condition under which the droplets were incubated anaerobically at 37° C. in modified Gifu Anaerobic Medium; B) with the addition of the antibiotic gentamicin (50 µg/mL) to the media at time zero; C) anaerobically at 39° C.; and D) aerobically (in the presence of oxygen) at 37° C. FIGS. 7A-7D shows *E. coli* growth measured in the plate reader on the top row, and *E. coli* growth measured from the mixed bacterial community in droplets on the bottom row. (FIGS. 7A-7D). The results depicted in FIGS. 7A-7D confirm that *E. coli* is sensitive to gentamicin (FIG. 7B), and that *E. coli* is a facultative anaerobe; it can grow both anaerobically and aerobically (FIGS. 7A and 7D); both of these observations are common knowledge. This demonstrates the ability to grow bacteria from a mixed community in different conditions and detect differences between them: adding antibiotics to the media tests antibiotic susceptibility, which has clinical relevance as antibiotic resistance has rapidly become a problem around the world. Isolating bacteria in droplets and then measuring their growth rates under different conditions (such as the addition of antibiotics) enables testing how an individual bacteria responds to a condition, without confounding factors or emergent effects that arise from growing in a community. (FIGS. 7A-7D).

Example 3: Measuring Growth Rates from a Full Fecal Community in Droplets

Bacteria present in a stool sample were isolated in droplets, according to the methods detailed in Example 1. A majority of the bacteria from the human gut microbiota that are present in stool were captured. This data is presented in the genus column for control_b and control_d entries, showing that of the bacteria present within the original fecal community (i.e., control_d), over 84% of the genera were grown in droplets. This is in contrast with the control_b that shows in a traditional batch culture (all bacteria grown together, no isolation within droplets), only 42% of the genera were able to grow. The subsequent rows provide growth under other conditions that were conducted on the full community, all grown in droplets. o2=grown in the presence of oxygen, ph=grown at a pH of 5.5 (normal media is pH 7), salt=grown with 2.5% salt, temp=grown at 39° C. (compared with 37° C.). These conditions were chosen as biologically relevant conditions that exist in gradients along the human gastrointestinal tract.

TABLE 1

|  | Kingdom | Phylum | Class | Order | Family | Genus | otus | |
|---|---|---|---|---|---|---|---|---|
| control_b | 0.5 | 0.666667 | 0.7 | 0.636364 | 0.652174 | 0.424242 | 0.238245 | Batch culture |
| control_d | 0.5 | 0.833333 | 0.9 | 0.818182 | 0.913043 | 0.848485 | 0.620690 | Droplet culture |
| o2 | 1 | 1 | 1 | 0.909091 | 0.956522 | 0.909091 | 0.642633 | |

TABLE 1-continued

|      | Kingdom | Phylum   | Class | Order    | Family   | Genus    | otus     |
|------|---------|----------|-------|----------|----------|----------|----------|
| ph   | 1       | 1        | 1     | 0.909091 | 0.956522 | 0.878788 | 0.673981 |
| salt | 1       | 1        | 1     | 0.909091 | 0.913043 | 0.818182 | 0.539185 |
| temp | 0.5     | 0.833333 | 0.9   | 0.818182 | 0.826087 | 0.757576 | 0.570533 |

Growth Rate Data from Full Fecal Community

Figure 8A:
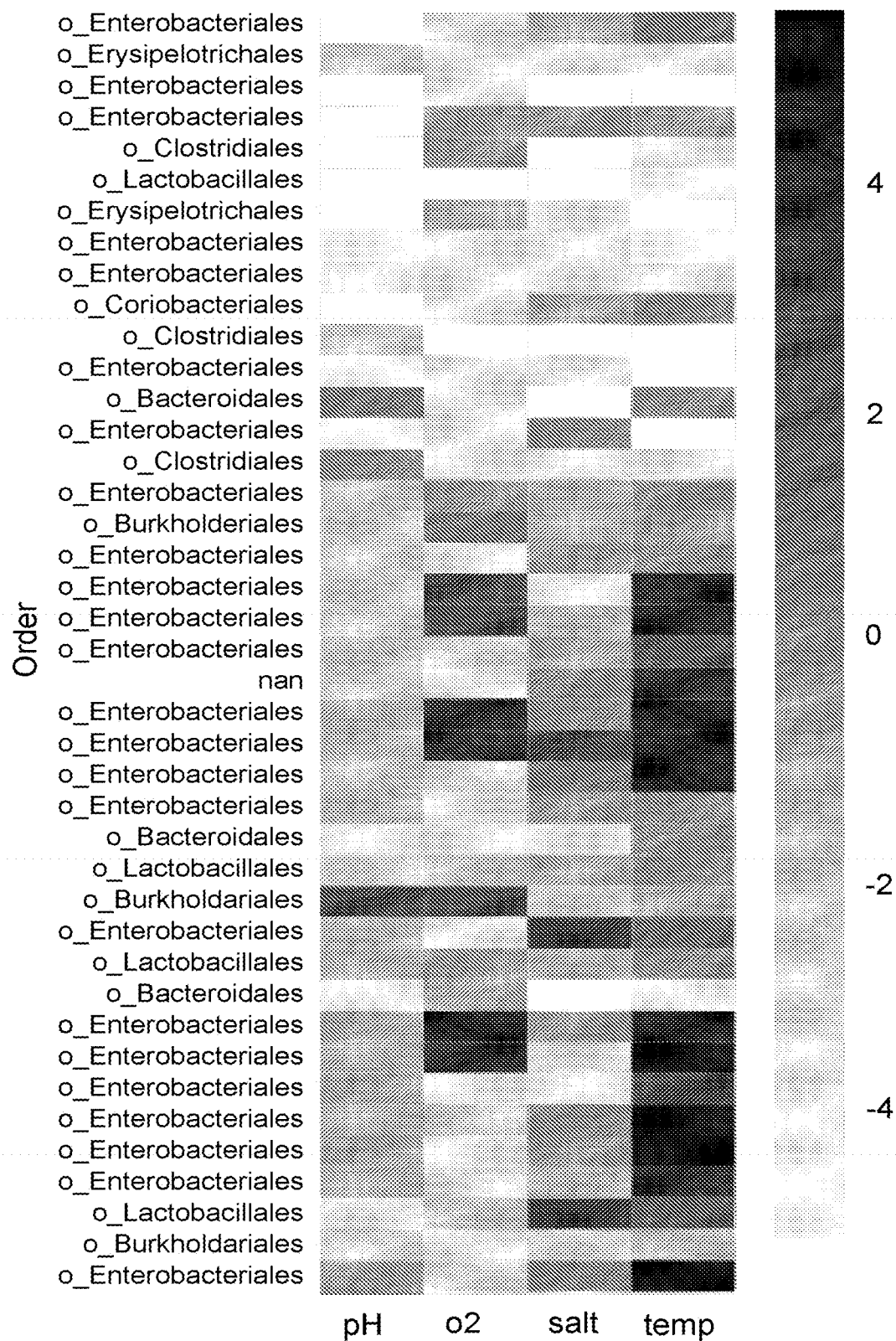
FIGS. 8A-8B show growth rate data from a full fecal community of individual bacteria at the order level, relative to the control growth rate provided in Table 1.
Figure 8B:
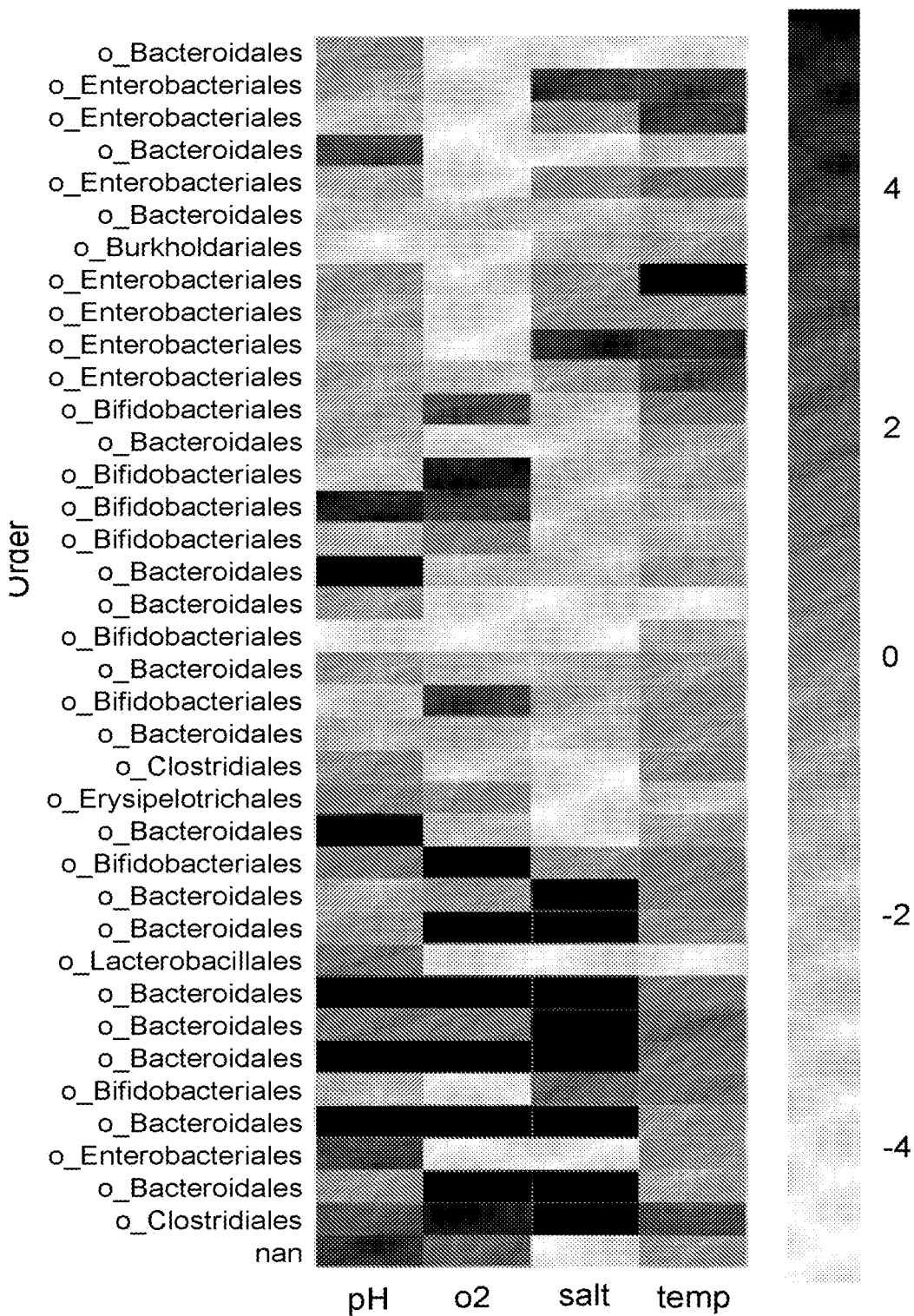

FIGS. 8A-8B provide growth rate data from a full fecal community, relative to the control growth rate under each of the following conditions: 02=grown in the presence of oxygen, ph=grown at a pH of 5.5 (normal media is pH 7), salt=grown with 2.5% salt, temp=grown at 39° C. (compared with 37° C.). The darker red indicates a faster growth rate under those conditions, while the darker blue indicates that the growth rate was slower at that condition than in the control. Grey boxes indicate missing values, or that there was no growth for that individual bacterial order under the corresponding condition. Each row indicates individual bacteria that are labelled at the order level. The data from FIGS. 8A-8B are summarized in Table 2, which shows that most of the taxa lost are lost due to growth in the presence of oxygen (# taxa lost). This is not unexpected, because the large intestine (where most of the gut bacteria are found) is known to be anaerobic, and many of these bacteria are known to be obligatory anaerobes.

TABLE 2

| condition    | # taxa lost | # taxa lower growth rate | # taxa higher growth rate |
|--------------|-------------|--------------------------|---------------------------|
| pH 5.5       | 3           | 58                       | 16                        |
| o2           | 25          | 30                       | 22                        |
| 2.5% salt    | 18          | 39                       | 17                        |
| 39° C. (temp)| 7           | 30                       | 36                        |

Example 4: Identifying Antagonistic Interactions Between Bacteria in Co-Culture Droplets Bacteria present in the gut were obtained from a human stool sample and resuspended in BHI Media. Fluorescently labeled (GFP) *E. coli* (strain MG1655) was added to the gut bacteria culture. The GFP-labeled *E. coli* and a random gut bacterium were encapsulated in droplets of BHI media surrounded by oil (oil-phase). (FIG. 4A). The co-cultured droplets were incubated under anaerobic conditions at 37° C. for 24 hours. The droplets were then sorted based on fluorescence of the *E. coli* using Fluorescence Activated Cell Sorting (FACS). (FIG. 4B.) Droplets without any fluorescence after incubation at 24 hours, but which exhibited growth of a non-fluorescent bacterial strain indicate that those gut bacterial strains inhibit the growth of the fluorescent *E. coli*. (FIG. 4E). These results provide a method to identify bacterial inhibitors of a target bacteria, such as *E. coli*, and can be applied to other bacterial strains, including pathogenic strains, such as enterohemorrhagic *E. coli* (EHEC), to identify bacterial strains present in the human gut that may prevent pathogenic bacteria from colonizing in the gut.

TABLE 3

Disclosed Nucleic Acid Sequences

| SEQ ID NO: 1 | Forward primer sequence for 16S V4 rRNA GTGCCAGCMGCCGCGGTAA |
|---|---|
| SEQ ID NO: 2 | Reverse primer sequence for 16S V4 rRNA GGACTACHVGGGTWTCTAAT |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method for measuring the growth rate of a bacterial strain from a mixed microbial community, comprising:
   (a) isolating a single bacterium by encapsulating the bacterium in an aqueous droplet surrounded by an oil-phase to obtain an encapsulated bacterium;
   (b) incubating the encapsulated bacterium under conditions appropriate for growth to obtain a single encapsulated bacterial strain;
   (c) extracting DNA from the encapsulated bacterial strain at various time points during incubation;
   (d) measuring:
      (i) a quantity of total DNA extracted from each of the various time points using quantitative Polymerase Chain Reaction ("qPCR") via primers that target a variable region within a conserved gene sequence; and
      (ii) a relative abundance of the encapsulated bacterial strain in the mixed microbial community at each time point through sequencing of the same variable region as in (i) using the same primers as in (i); and
   (e) generating a growth curve of the bacterial strain over the various time points by combining the measurements obtained in (d) at each of the various time points, thereby obtaining the growth rate of the bacterial strain.

2. A method for assessing the potential for a bacterial strain from a mixed microbial community to develop resistance to an antibiotic drug, comprising:
   (a) isolating a single bacterium by encapsulating the bacterium in an aqueous droplet surrounded by an oil-phase to obtain an encapsulated bacterium;
   (b) incubating the encapsulated bacterium in the presence of an antibiotic drug, under conditions appropriate for growth to obtain a single encapsulated bacterial strain;
   (c) extracting DNA from the encapsulated bacterial strain at various time points during incubation;
   (d) measuring:
      (i) a quantity of total DNA extracted from each of the various time points using quantitative Polymerase Chain Reaction ("qPCR") via primers that target a variable region within a conserved gene sequence; and
      (ii) a relative abundance of the encapsulated bacterial strain in the mixed microbial community at each time point through sequencing of the same variable region as in (i) using the same primers as in (i); and
   (e) generating a growth curve of the bacterial strain over the various time points by combining the measurements obtained in (d) at each of the various time points, wherein a lower growth rate compared to the growth rate in the absence of the antibiotic drug suggests that the bacterial strain is not resistant to the antibiotic drug.

3. A method for characterizing the microflora in a patient's gut, comprising:
   (a) isolating each bacterium within a patient's stool sample by individually encapsulating the bacterium in an aqueous droplet surrounded by an oil-phase to obtain individually encapsulated bacteria;
   (b) incubating each encapsulated bacterium under conditions appropriate for growth to obtain encapsulated bacterial strains;
   (c) extracting DNA from each encapsulated bacterial strain at various time points during incubation;
   (d) measuring:
      (i) a quantity of total DNA extracted from each of the various time points using quantitative Polymerase Chain Reaction ("qPCR") via primers that target a variable region within a conserved gene sequence; and
      (ii) a relative abundance of the encapsulated bacterial strain in the microflora at each time point through sequencing of the same variable region as in (i) using the same primers as in (i); and
   (e) generating a growth curve of each encapsulated bacterial strain over the various time points by combining the measurements obtained in (d) at each of the various time points, thus characterizing the microflora in the patient's gut.

4. The method of any claim 1, wherein isolation of the bacterium via encapsulation is random.

5. The method of claim 1, wherein the encapsulated bacterium is incubated under anaerobic conditions.

6. The method of claim 1, wherein the aqueous droplet encapsulating the bacterium comprises nutrient-rich culture media.

7. The method of claim 6, further comprising modifying the nutrient-rich culture media by changing the pH from about 7.0 to about 5.5 or including about 2.5% salt (NaCl).

8. The method of claim 1, wherein the aqueous droplet encapsulating the bacterium comprises defined media.

9. The method of claim 1, wherein the aqueous droplets encapsulating bacteria are incubated at 37° C.

10. The method of claim 1, wherein the aqueous droplets encapsulating bacteria are incubated at 39° C.

11. The method of claim 1, wherein the primers target a variable region within conserved gene sequence 16s ribosomal RNA ("rRNA"), the primers comprising: GTGCCAGCMGCCGCGGTAA (SEQ ID NO:1) and GGACTACHVGGGTWTCTAAT (SEQ ID NO:2).

12. The method of claim 1, wherein the growth curve is generated by multiplying the relative abundance sequencing data obtained for each of the various time points by the quantitative qPCR data obtained for the corresponding time point.

* * * * *